US007650991B2

(12) United States Patent    (10) Patent No.: US 7,650,991 B2
Hester et al.                 (45) Date of Patent:    Jan. 26, 2010

(54) SURGICAL SCREW DISPENSER

(75) Inventors: Peter Hester, Revesby (AU); John Peter Nielsen, 17 Hazeldean Avenue, Kenthurst, New South Wales (AU); Rhett James Kentwell, Oyster Bay (AU)

(73) Assignee: John Peter Nielsen, Kenthurst, New South Wales (AU)

( * ) Notice: Subject to any disclaimer, the term of this patent is extended or adjusted under 35 U.S.C. 154(b) by 429 days.

(21) Appl. No.: 11/159,987

(22) Filed: Jun. 23, 2005

(65) Prior Publication Data
US 2005/0261691 A1    Nov. 24, 2005

(51) Int. Cl.
B65D 85/24 (2006.01)
A61B 17/00 (2006.01)

(52) U.S. Cl. .................. 206/339; 606/104
(58) Field of Classification Search .......... 206/339, 206/345–347, 370, 338; 81/120–125, 451–458; 433/172–174; 606/73, 96, 104
See application file for complete search history.

(56) References Cited

U.S. PATENT DOCUMENTS

| 1,779,339 | A | * | 10/1930 | Sokoloff | 81/452 |
| 2,723,694 | A | * | 11/1955 | Ross | 81/451 |
| 2,985,208 | A | * | 5/1961 | Hibbard et. al. | 81/452 |
| 3,901,298 | A | * | 8/1975 | Eby | 81/455 |
| 4,955,476 | A | * | 9/1990 | Nakata et al. | 206/346 |
| 5,065,649 | A | * | 11/1991 | Evers et al. | 81/458 |
| 5,129,292 | A | * | 7/1992 | Albert | 81/452 |
| 5,368,160 | A | * | 11/1994 | Leuschen et al. | 206/339 |
| 5,775,514 | A | * | 7/1998 | Lin | 206/347 |
| 6,328,746 | B1 | * | 12/2001 | Gambale | 606/104 |
| 7,007,798 | B2 | * | 3/2006 | Happonen et al. | 206/339 |
| 2002/0166421 | A1 | | 11/2002 | Bowerman | |

FOREIGN PATENT DOCUMENTS

| AU | 5548699 | 2/2000 |
| DE | 3006648 A1 | 8/1981 |
| WO | WO 0007510 A | 2/2000 |

* cited by examiner

Primary Examiner—Bryon P Gehman
(74) Attorney, Agent, or Firm—Michael Bergman; Bergman & Song LLP

(57) ABSTRACT

A surgical screw container includes at least one recess which is adapted to receive therein a screw with a head and a threaded shank. The recess has an opening at one end to allow the screw to pass into or out of the recess. The recess is arranged so that the screw lies within the recess with the head of the screw facing the opening. The recess includes a detent device for retaining the screw within the container. The insertion of a screwdriver shaft into the recess releases the screw.

23 Claims, 15 Drawing Sheets

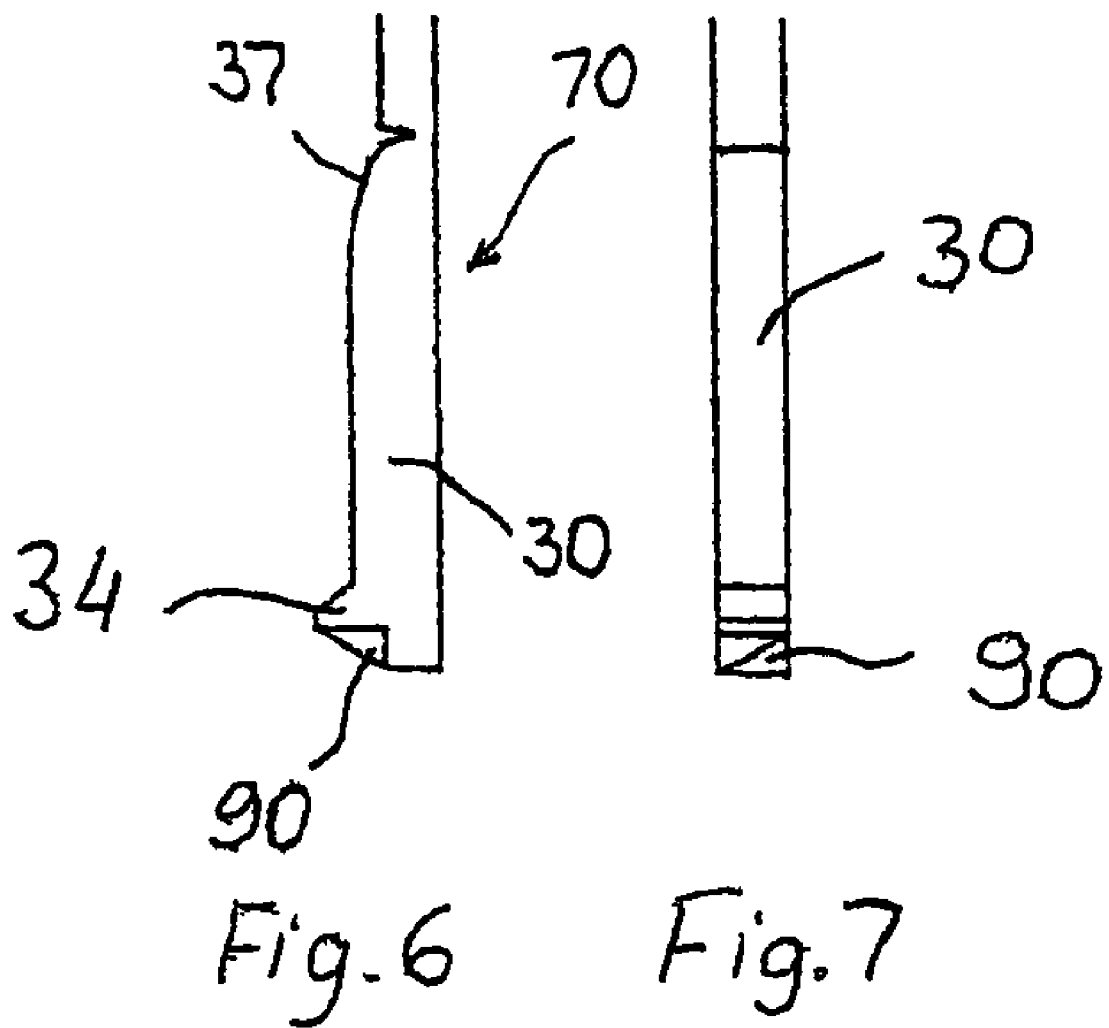

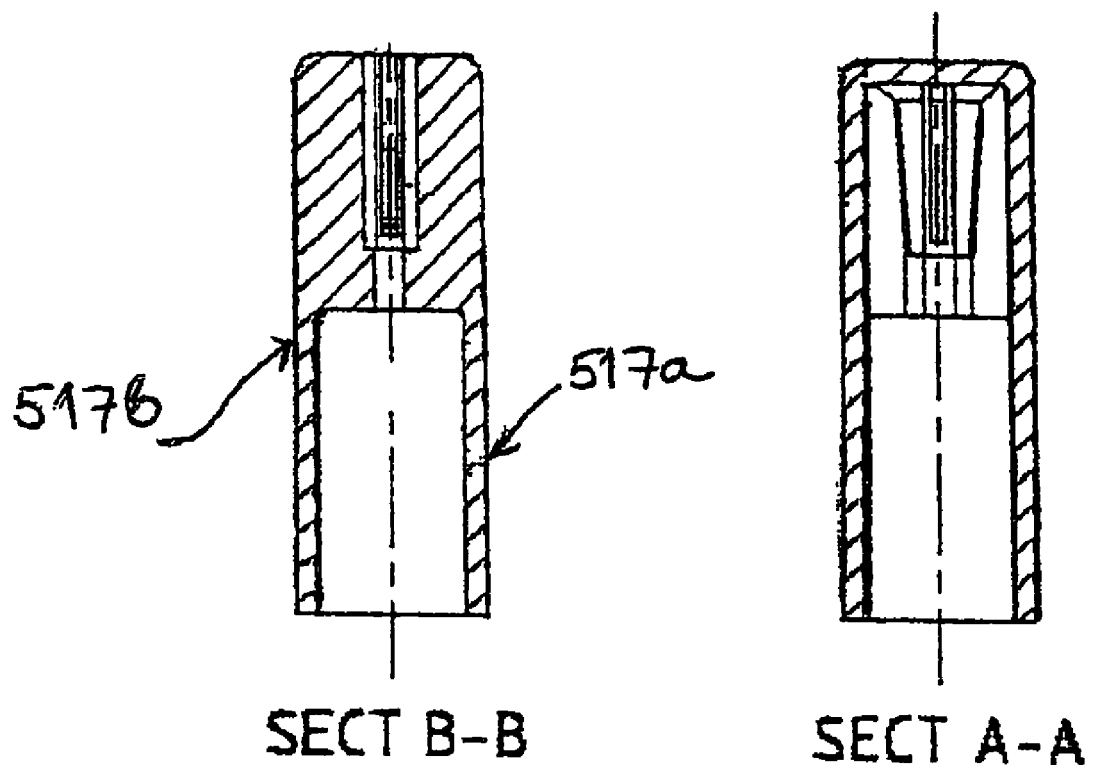

SECT D-D    SECT C-C

SURGICAL SCREW DISPENSER

CROSS REFERENCE TO RELATED APPLICATIONS

The present application claims priority to PCT Application No. PCT/AU2003/001718 filed Dec. 23, 2003 and titled "Surgical Screw Dispenser" which in turn claims priority to Australian Patent Application No. 2002953567 filed Dec. 24, 2002 and titled "Surgical Screw Dispenser," the disclosure of each of the foregoing being herewith incorporated by reference in its entirety.

FIELD OF THE INVENTION

This invention relates to a container for screws. It relates, more particularly, to a device for the storage and dispensing of surgical screws.

BACKGROUND OF THE INVENTION

Surgical screws are widely used in the field of surgery; the most common uses include plastic and reconstructive surgery, dentistry, and orthopaedic surgery.

The diameter of the heads of surgical screws vary but can be in the range of 0.8 mm to 3 mm and possibly upto 10 mm. Problems relating to storage and dispensing of surgical screws can arise due to this relatively small diameter.

A conventional container for the storage of surgical screws has a shell of plastic containing a series of elongated recesses into which screws may be placed. A lid can be hinged to the shell for covering the shell in a closed position. The lid is movable to an open position to allow access to the screw. While such a container provides for individual storage locations for each screw, once the lid is open screws can fall out of the container. As a consequence, the screws become contaminated and can no longer be used unless re-sterilised.

SUMMARY OF THE INVENTION

The present invention resides in a surgical screw container including
 at least one recess which is adapted to receive therein a screw having a head and a threaded shank, said recess having an opening at one end to allow said screw to pass into and out of said recess, said recess being such that said screw lies within said recess with said head of said screw facing said opening,
 retaining means for retaining said screw within said container, said retaining means being disposed within said recess and being releasable by insertion of a screwdriver shaft into said recess through said opening to allow withdrawal of said screw through said opening after said screwdriver engages said screw.

Preferably said recess includes means to receive said shank of said screw.

Preferably said recess includes a sleeve portion for imposing a radial constraint on said screw.

In a preferred embodiment the sleeve portion has an opening which is smaller than the diameter of the head of the screw but larger than the diameter of the shank of the screw, the longitudinal axis of said opening being aligned with a longitudinal axis of the recess; and an abutting surface upon which the head of the screw rests.

Preferably said retaining means includes at least one elastically flexible finger extending longitudinally within said recess.

Preferably said finger has a free end provided with a lip and a contacting portion for contacting a screwdriver shaft, said lip being oriented so as to engage a portion of said screw.

In one preferred embodiment, the lip is adapted to engage the head of said screw to impose axial constraint on said screw.

In another preferred embodiment, the lip is adapted to engage a thread on said threaded shank.

Preferably the finger is movable away from the longitudinal axis of said recess upon said screwdriver being urged toward said screw.

Preferably, the container further includes means for locking said finger in spaced relation away from said screw.

In a preferred embodiment the finger is moveable between a locked position in which a screw is retained within said recess and an open position in which the screw may be removed from said recess.

Preferably, the means for locking includes a detent arrangement including at least one projection formed on the finger to interact with a complementary retaining recess formed on the wall of said screw-receiving recess, said complementary recess being spaced from said projection a distance such that said screw is free from interference with the finger when said finger is in its locked position.

The finger may be biased. Preferably the finger is biased to move into the locked position.

The finger may be frangible or breakable.

Preferably, said finger is formed in one piece with said recess.

Preferably, said sleeve is formed in one piece with said recess.

Preferably the container includes a plurality of fingers, said fingers being substantially equi-spaced around the screw-receiving recess.

Preferably said surgical screw container includes a body shell having an open box configuration for providing access for a sterilising medium.

Preferably said body shell includes an upper surface, two opposite side surfaces, a front surface, a back surface, and an open bottom, and said screw-receiving recess terminates at said upper surface.

Preferably an outer periphery of said screw-receiving recess is provided with a frusto-conical region terminating to said upper surface of said surgical screw container.

In a preferred embodiment said finger includes a front surface, a back surface, and two side surfaces, a longitudinal portion of each said side surface of said finger being separated from a surface of said container at which said finger terminates.

In one preferred embodiment said screw-receiving recess and said retaining means are manufactured separately from said body shell as a stand alone screw-holding unit and then subsequently attached to said body shell in a succeeding manufacturing step.

Preferably said surgical screw container includes a plurality of said screw-holding units, said screw-holding units being arranged such as to reduce the size of said container.

The present invention also provides a surgical screw container including
 a screw receiving recess for receiving a screw, and
 orientation means for orientation of said screw relative to said recess.

In a further form, the present invention provides a surgical screw container including a screw receiving recess, said recess being adapted to receive a shank of a screwdriver, said screwdriver having a screw engaging tip, and orientation means for orientation of said screw engaging tip relative to said recess.

The present invention also provides a surgical screw container including a screw receiving recess for receiving a screw, said recess being adapted to receive a shank of a screwdriver, said screwdriver having a screw engaging tip, and means for relatively aligning said screw engaging tip with respect to the head of said screw.

Preferably said orientation means for orientation of said screw engaging tip of said screwdriver relative to said recess includes at least one axially extending groove formed on a wall of said screw receiving recess and matched with a guiding projection formed on the outer periphery of the shank of the screwdriver.

Preferably said orientation means for orientation of said screw relative to said recess includes means for engagement of the screw-driver receiving portion of said screw.

Preferably said container includes at least one label identifying the screws in the container.

Preferably said container includes means for marking the position of said label on said container.

Preferably said means for marking the position of said label includes a notch provided on said container.

BRIEF DESCRIPTION OF THE DRAWINGS

Embodiments of the invention will be described below, by way of example only, with reference to accompanying drawings in which:

FIG. 6 shows a detail front view of the lip of the finger of FIGS. 1 to 5, FIG. 7 shows a detail side view of the lip of FIG. 6, FIG. 16 is a cross-sectional view taken along line A-A of FIG. 15, FIG. 17 is a cross-sectional view taken along line B-B of FIG. 15.

DETAILED DESCRIPTION OF THE EMBODIMENTS

Figures 1, 2:
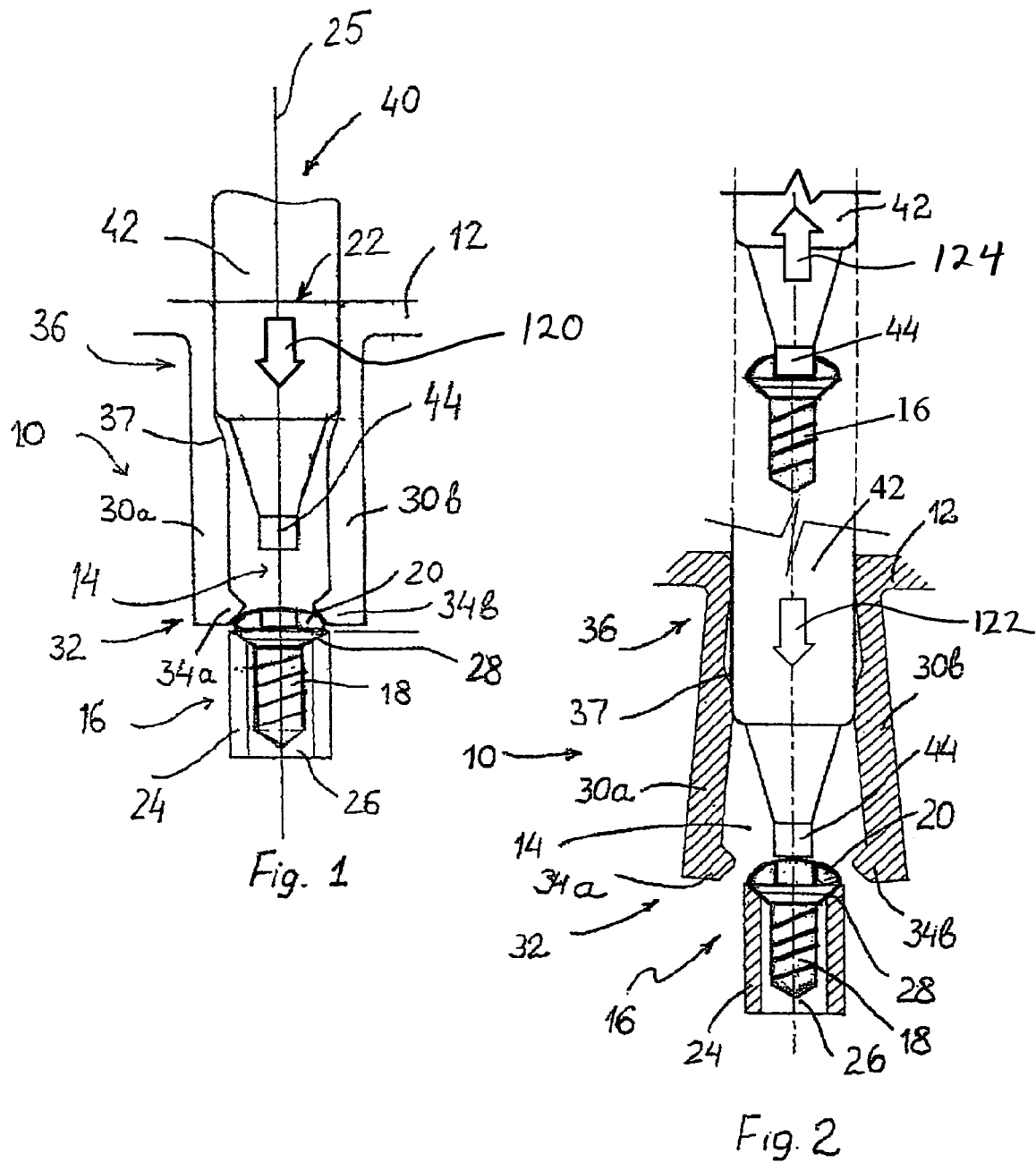
FIG. 1 is a schematic view of a surgical screw container according to a first embodiment of the present invention.
FIG. 2 shows the container of FIG. 1 in a dispensing position, FIG. 3 a schematic view of a surgical screw container according to a second embodiment of the present invention.

FIG. 1 shows screwdriver shaft 42 being moved 120 into recess 14. FIG. 2 shows screwdriver shaft 42 being moved 122 further into recess 14, and thereafter being withdrawn 124 from recess 14.

FIGS. 1 and 2 depict a schematic view of a container 10 suitable for the storage of surgical screws 16. FIG. 1 illustrates the container 10 in a locked condition. The container 10 has a one-piece body shell 12 with a screw-receiving recess 14 adapted to receive a surgical screw 16, which has a threaded shank 18 and a head 20. The recess 14 includes an opening 22 through which the screw 16 passes into and out of the recess 14.

The screw 16 is received within a sleeve 24 having a substantially cylindrical opening 26 which is smaller than the diameter of the head 20 of the screw 16 but larger than the diameter of the shank 18. The central longitudinal axis 25 of the opening 26 is aligned with the longitudinal axis of the recess 14. The sleeve 24 has an abutting surface 28 upon which the head 20 of the screw 16 rests.

The sleeve 24 and the opening 22 are arranged such that the screw 16 lies within the recess 14 with the head 20 of the screw facing the opening 22.

Extending longitudinally within the recess 14 are elastically flexible fingers 30a and 30b. Although two fingers are illustrated in FIGS. 1 to 4, it will be appreciated by those skilled in the art that any number of fingers can be employed in the present invention.

In a preferred embodiment the container includes at least two fingers, and the fingers are substantially equi-spaced around the recess.

Each finger has a free end 32 provided with a lip 34 oriented towards the longitudinal axis of the recess 14 to engage the head 20 of the screw 16 to impose an axial constraint on the screw and thus maintain the screw 16 in the sleeve 24, until it is desired to remove the screw 16.

As can be seen from FIG. 2, the free end of the finger 30 is movable away from the central longitudinal axis 25 of the recess 14 when a screwdriver 40 is urged towards the screw 16 through the opening 22. To this end, the finger 30 is provided with a contacting portion 36 adapted to guide a screwdriver shaft 42 towards the screw 16, and a tapered or converging surface 37 which will allow the finger 30 to be pushed radially away from the central longitudinal axis 25 of the recess 14.

Figure 8:
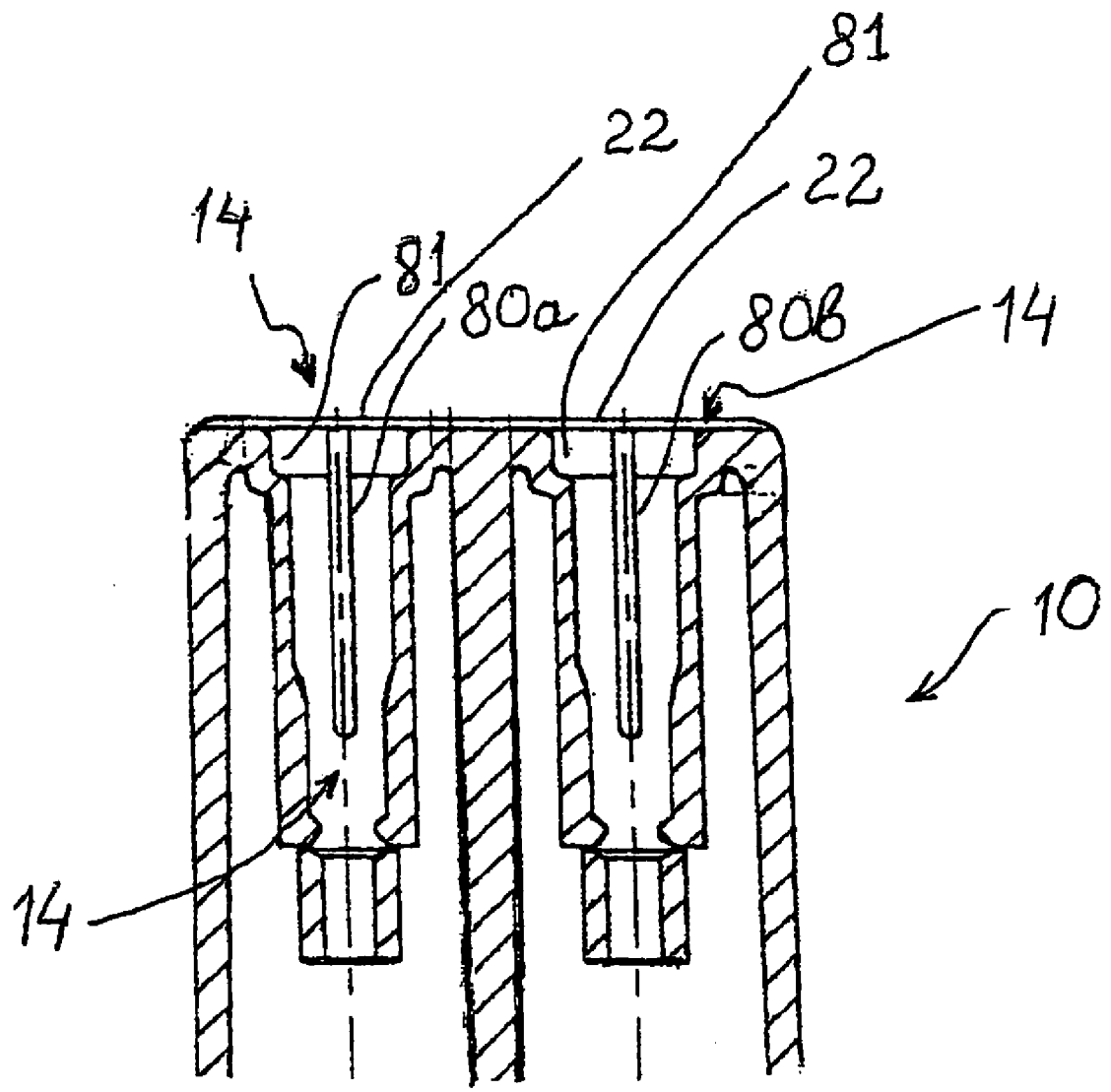
FIG. 8 shows guiding grooves provided on the wall of the container of FIGS. 1 to 5 for orientation of the screwdriver relative to the screw-receiving recess.
Figure 11:
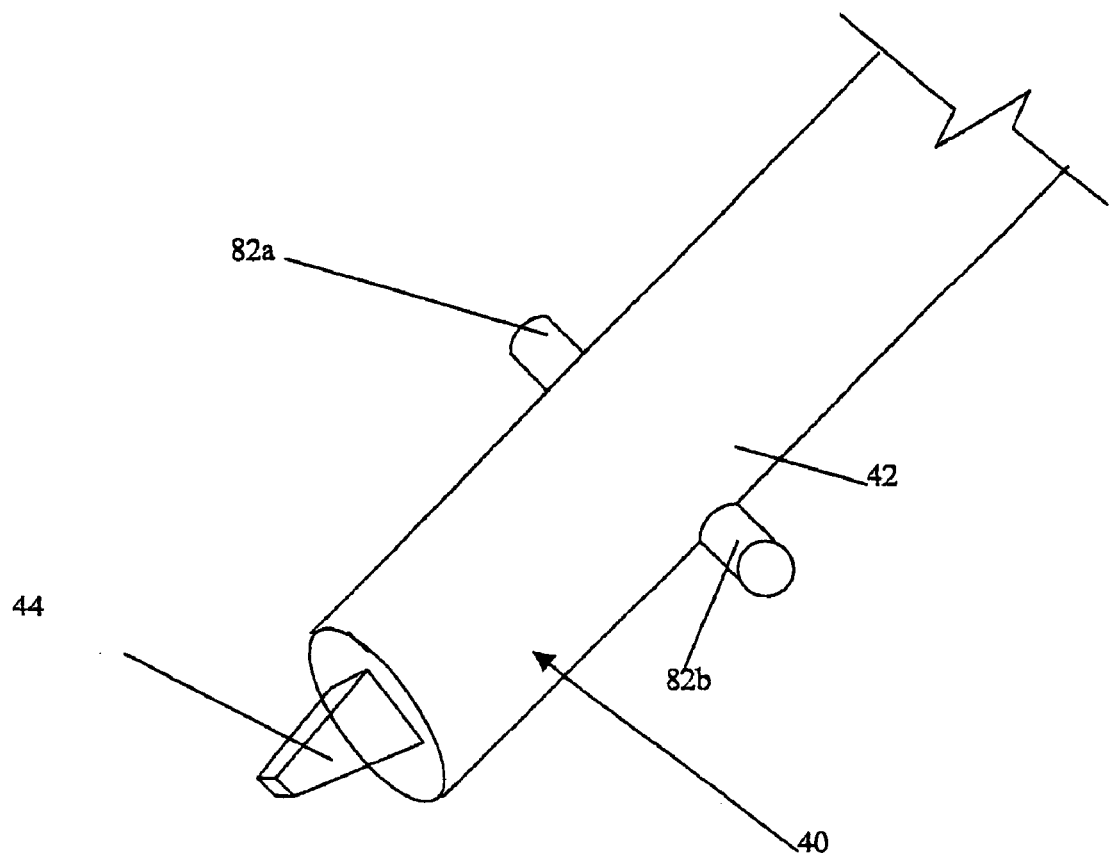
FIG. 11 illustrates a perspective view of a screw driver shank and tip.

As shown in FIG. 8, the container 10 includes a pair of axially extending guiding grooves 80a, 80b formed on a wall 54 of the screw-receiving recess 14 and matched with a pair of guiding projections 82a, 82b, see FIG. 11, which protrude from the outer periphery of the screwdriver shaft 42. The grooves 80 are adapted to slidably receive the projections 82 formed on the screwdriver shaft 42 so that the screwdriver is capable of sliding within the recess by travelling the projections 82a, 82b along the grooves 80a, 80b respectively. As a result, the screw-engaging tip 44 of the screwdriver 40 is orientated relative to the screw-receiving recess 14 such that the screwdriver 40 can engage the head 20 of the screw 16.

As can be seen from FIGS. 6 and 7, the lip 34 of the finger 30 is provided with a recess 90 adapted to engage the screwdriver receiving portion of the head 20 of the screw 16 thereby providing means for orientation of the head 20 of the screw 16 relative to the screw-receiving recess 14.

Figure 9:
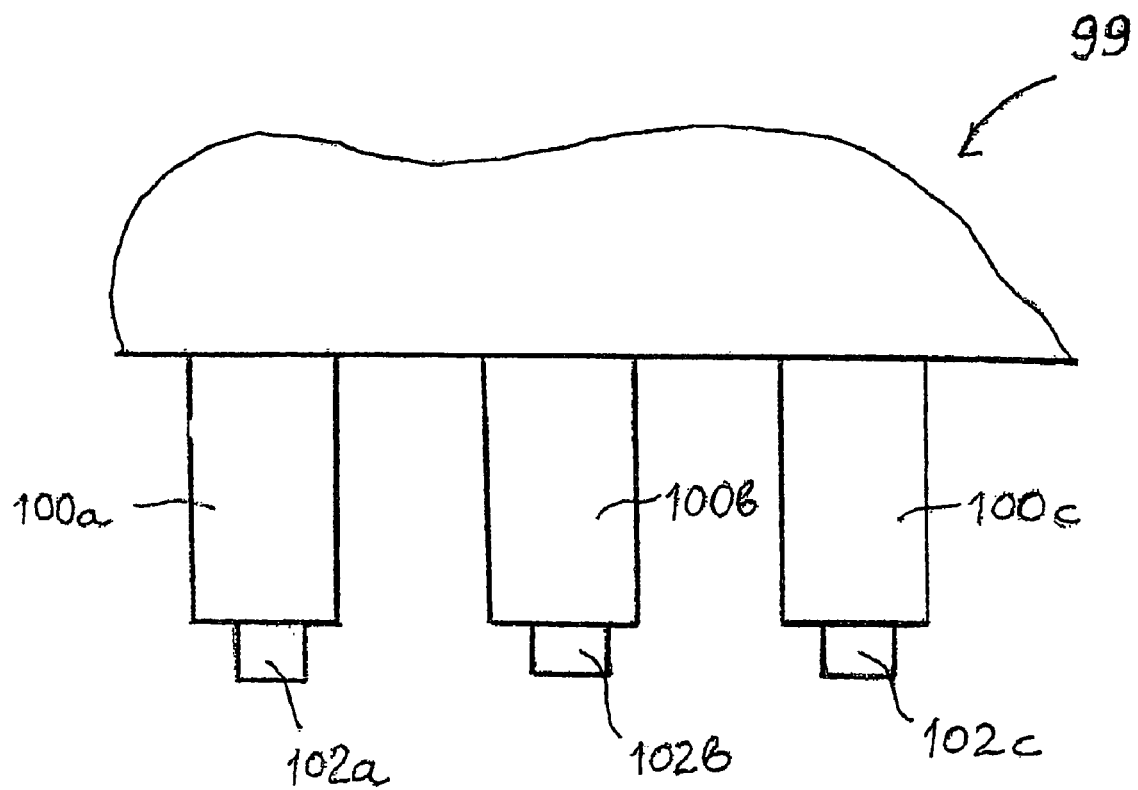
FIG. 9 shows a device for loading the container of FIG. 1.

FIG. 9 shows a jig 99 for loading the container 10 with surgical screws 16. The jig 99 includes a plurality of screw-carrying projections 100. In a preferred embodiment the number and position of the screw-carrying projections 100 correspond to the number and position of the screw-receiving recesses 14. If the recesses are in an in-line relationship the tool of FIG. 9 can be used. If another relationship, such as for example that four recesses are provided at the four apexes of a square, then the four prongs on the jig 99 can also be located in the same spaced relationship.

The jig 99 is adapted to allow the projection 100 to be inserted into the screw-receiving recess 14 through the opening 22 while preventing said projection from interfering with the fingers 30.

Each projection 100 includes a screw engaging tip 102 onto which a screw can be loaded. The screw-engaging tip 102 is orientated relative to the screw-receiving recess 14 such that the head 20 of the screw 16 can pass through the opening formed by recess 90 provided on the lip of the finger 30. As a result, the head 20 of the screw 16 is orientated relative to the guiding grooves 80 such that the screw engaging tip 44 of the screwdriver 40 is aligned with respect to the head 20 of the screw 16.

In use, a plurality of screws 16 are loaded onto the screw-engaging tips 102 of the projections 100. The projections 100, with the screws 16 protruding therefrom, are then inserted into the screw-receiving recesses 14 through the openings 22 of the container 10. Once the screw 16 has been loaded into the screw-receiving recess 14, the screw-engaging tip 102 is released, and the projections 100 are lifted from the container 10.

When it is desired to use a surgical screw, a screwdriver 40 is inserted into the opening 22 with projections fitting into the grooves 80 of the screw-receiving recess 14 and urged towards the head 20 of the screw 16. As a result of the pressure exerted by the shaft 42 of the screwdriver 40 against the converging surface 37 of the finger 30, the finger 30 flexes outward, and the lip 34 moves away from the longitudinal axis of the recess 14 thereby releasing the screw 16.

Figure 13:
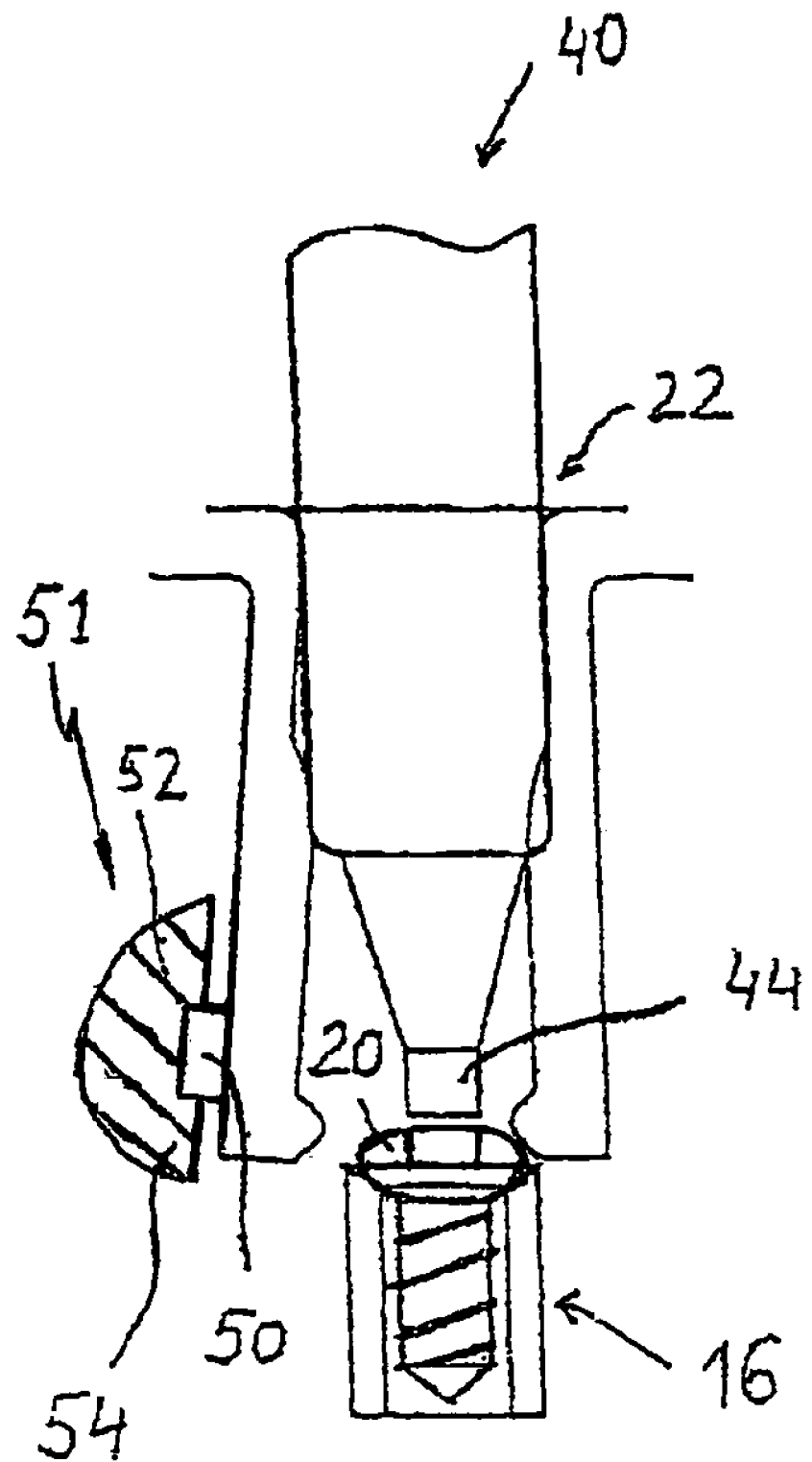
FIG. 13 illustrates a container similar to that of FIG. 1, with means to hold the fingers in the open condition.

If desired, as is illustrated in FIG. 13, the fingers 30a and 30b can be locked in their open condition away from the screw 16 by means of a detent arrangement 51 which includes a projection 50 formed on the finger 30 and a complementary recess 52 formed on a wall 54 of the recess 14. The recess 52 is spaced from the projection 50 a distance such that the screw 16 is free from interference from the finger 30 when the finger is in its open condition. For ease of illustration in FIG. 13, only the left side finger 30a is depicted as having moved. Finger 30b would also move simultaneously with finger 30a.

Figure 5:
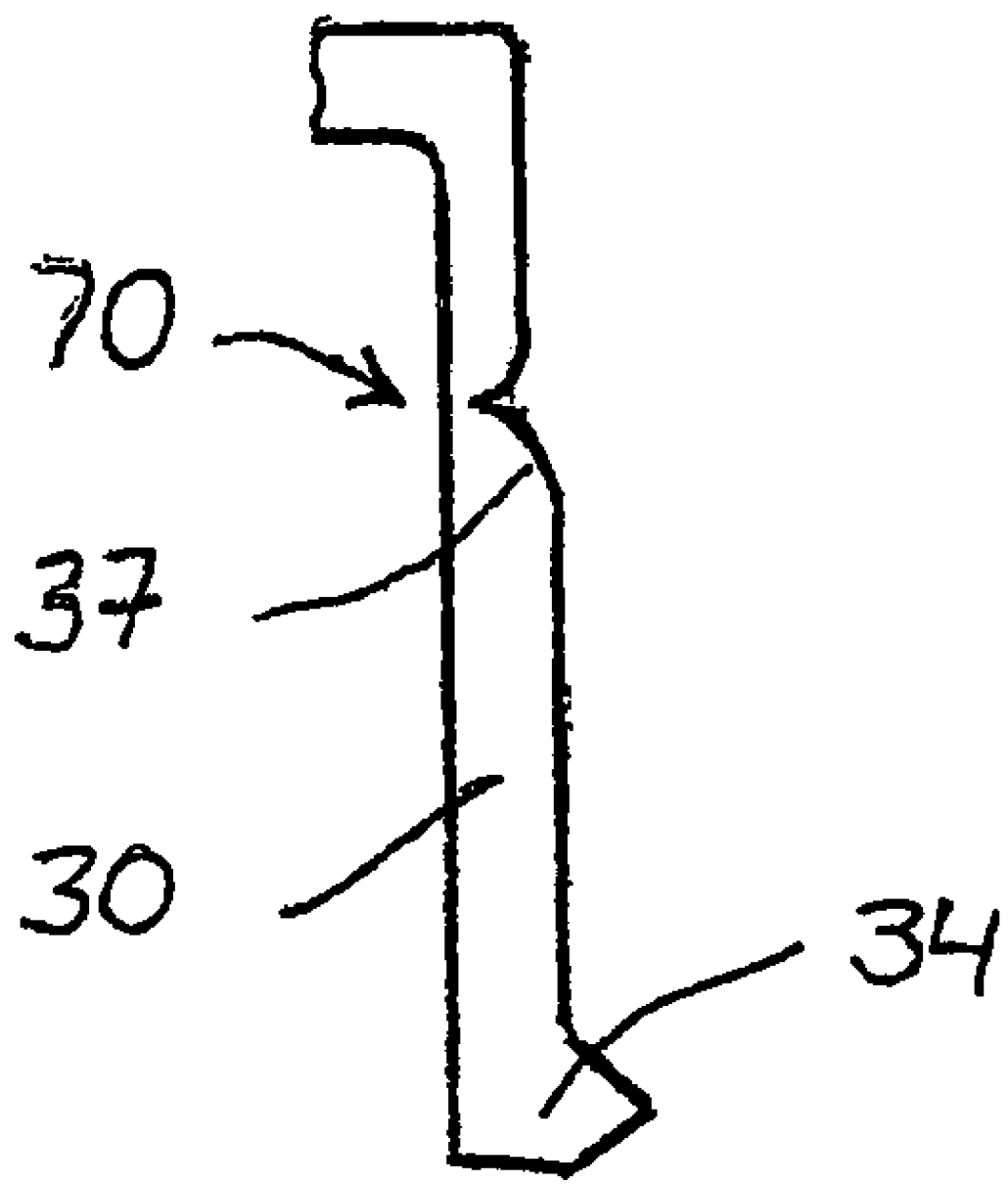
FIG. 5 shows a modified form of the finger of FIGS. 1 to 4.

As can be seen from FIG. 5, alternative arrangements for preventing the finger from moving back into the locked position can include providing the fingers 30 with a frangible portion 70, above the converging surface 37, whereby the fingers 30 partially or wholly fracture so that the fingers 30 will lose their elasticity once a screw driver shaft 42 has been inserted. If it is important to ensure the fingers 30 remain attached to the container, then only partial fracture would be required. If remaining connected is unimportant, then a complete dismemberment can be utilised. By partial or whole fracturing of the fingers 30, there will result a single use cartridge, dispenser or container which will ensure that re-use will be minimised.

The screwdriver 40 is inserted into the opening 22 until a tip 44 of the screwdriver 40 engages the head 20 of the screw 16. The screwdriver 40 is then lifted out of the recess 14 through the opening 22 with the screw 16 affixed to the tip 44 of the screwdriver. The screwdriver is then ready for use to insert the screw into a desired location.

Figures 3, 4:
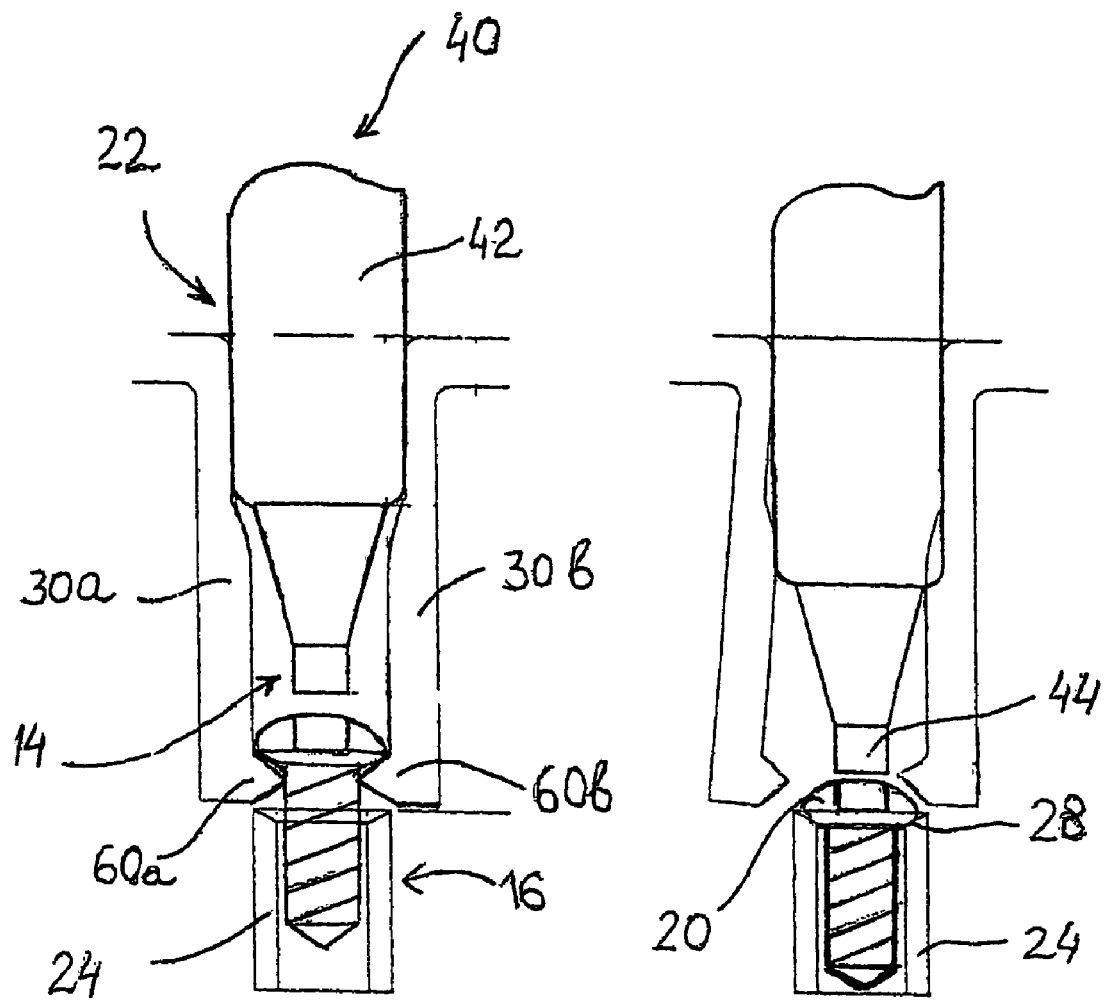
FIG. 4 shows the container of FIG. 3 in a dispensing position.

FIGS. 3 and 4 show a surgical screw container according to a second embodiment of the present invention. The embodiment of FIGS. 3 and 4 is similar to that of FIGS. 1 and 2, and like part have been like numbered.

In common with the first embodiment, the container of FIGS. 3 and 4 also has a screw-receiving recess 14, a sleeve 24, and a pair of fingers 30a and 30b. Each finger is provided with a tooth 60 adapted to engage the threaded shank of the screw 16. The fingers 30a and 30b can engage the threaded shank either by a frictional contact, or by having a soft tip protrude between adjacent threads, or a thin formation to protrude between adjacent threads.

As can be seen from FIG. 4, the insertion of the shaft 42 of the screwdriver 40 into the opening 22 causes the tooth 60 to move away from the threaded shank of the screw 16 thereby releasing the screw 16. The released screw 16 is then received within the sleeve 24 with the head 20 of the screw 16 finally resting on the abutting surface 28 of the sleeve 24. For ease of illustration in FIG. 4, only the left side finger 30a is depicted as having moved. Finger 30b would also move simultaneously with finger 30a.

Similarly to the first embodiment, the downward movement of the screwdriver 40 is continued until the tip 44 of the screwdriver engages the head 20 of the screw 16. Once the screw 16 is loaded onto the tip 44 of the screwdriver, the screw 16 can be removed from the container 10 through the opening 22.

The container 10 preferably includes a plurality of screw-receiving recesses to accommodate a plurality of screws respectively therein. Alternatively the container can have only a single recess to hold only a single screw.

Figure 10:
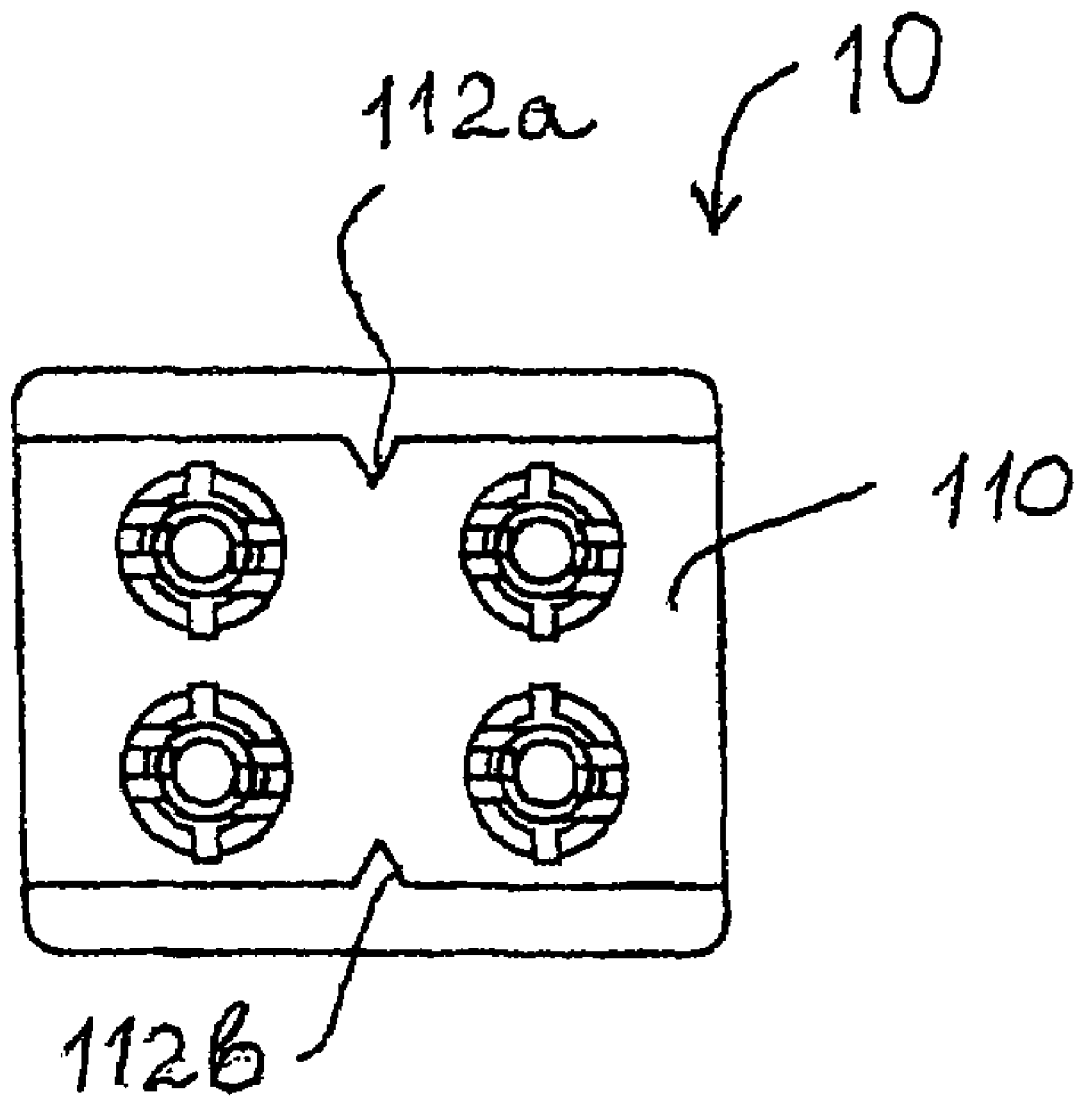
FIG. 10 shows a marking notch for positioning an identifying label on the container of FIG. 1.
Figure 12:
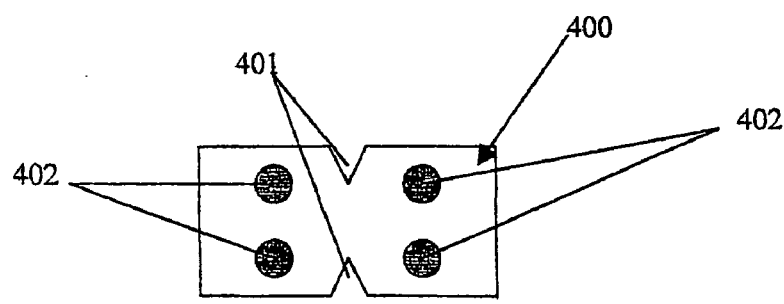
FIG. 12 illustrates a label for use with the container of FIG. 10.

The recesses may be marked with identifying labels such as the label 400 illustrated in FIG. 12, describing the size of the screws, etc. In a preferred embodiment shown in FIG. 10 the upper surface 110 of the container 10 is provided with a pair of marking triangular shoulders 112a, 112b for positioning label 400 which has corresponding notches 401 to match the shape of the shoulders 112a and 112b. The label 400 can be colour coded to correspond to predetermined sizes of screws and have a coloured region 402 which will overlie the recesses 14, so that a nurse or surgeon knows exactly where the recess 14 is located.

As can be seen in FIG. 8 the top rim of the recess 14 has a larger diameter portion 81, which is sized so that when a label overlies the top opening 22, and is then pierced when a screw driver 40 is inserted into the recess 14 so as to retrieve a screw, then the fragments of the label formed when the screw driver is inserted will be located within the larger diameter portion 81 so that the fragments will not obstruct the path of a screw being withdrawn from the recess 14.

FIGS. 14-21 illustrate a surgical screw container 500 according to a third embodiment of the present invention.

Figure 14:
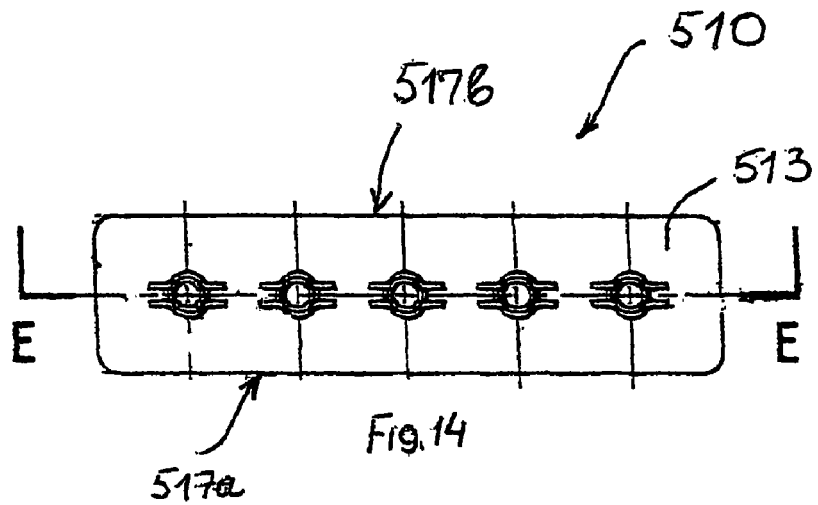
FIG. 14 is a top view of a surgical screw container according to a third embodiment of the present invention.
Figure 15:
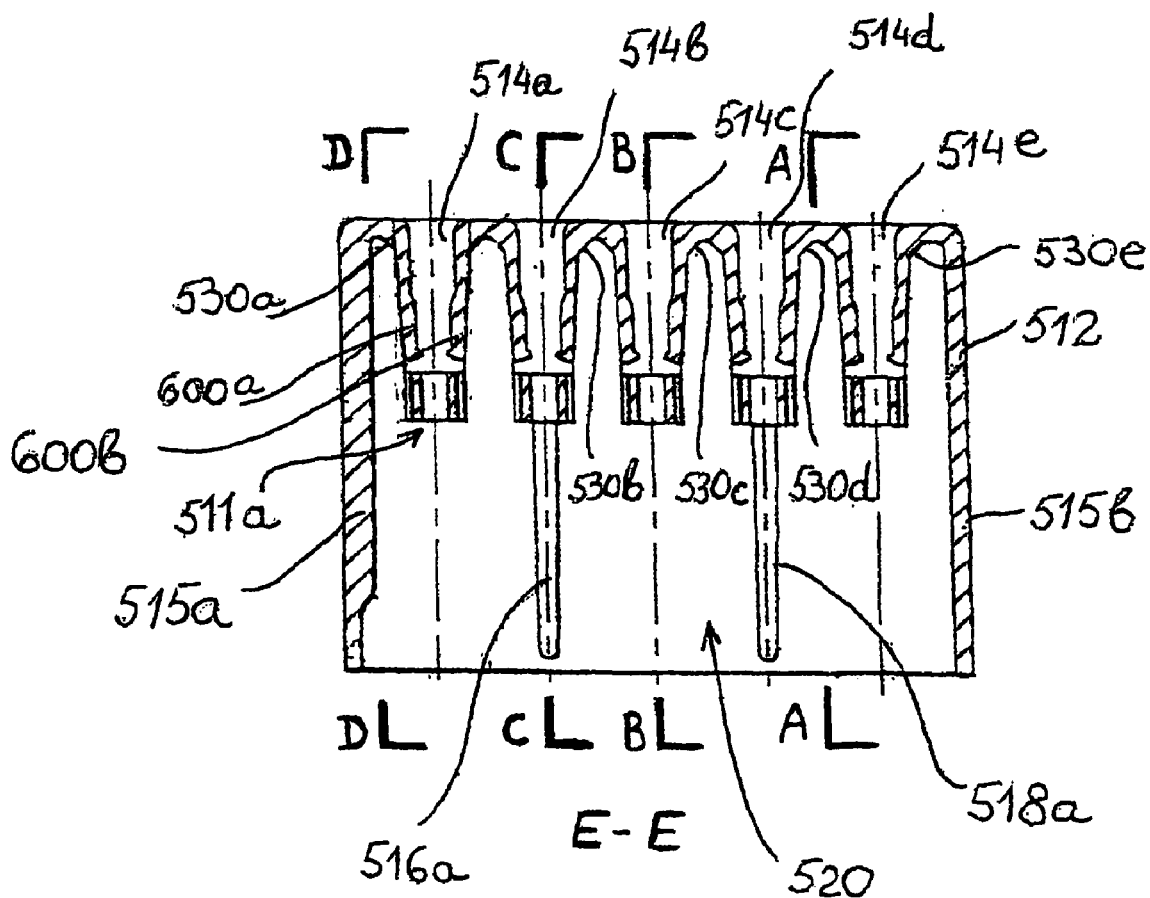
FIG. 15 is a cross-sectional view taken along line E-E of FIG. 14.
Figure 19:
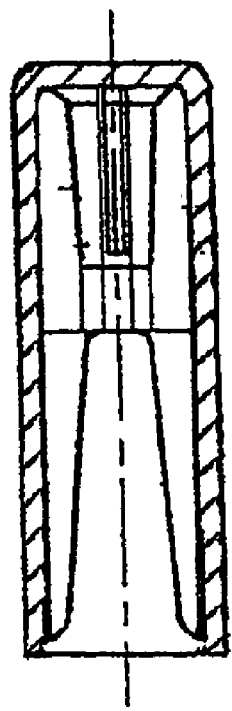
FIG. 19 is a cross-sectional view taken along line D-D of FIG. 15.
Figure 18:
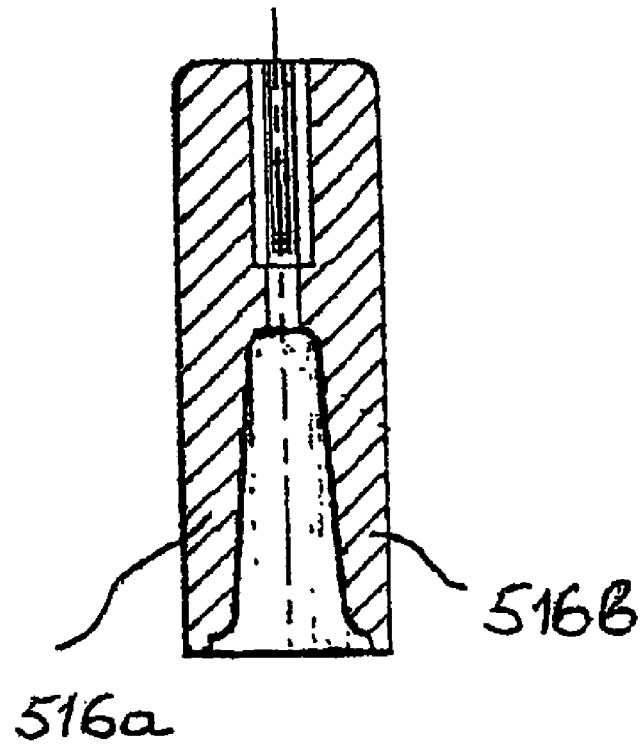
FIG. 18 is a cross-sectional view taken along line C-C of FIG. 15.
Figure 20:
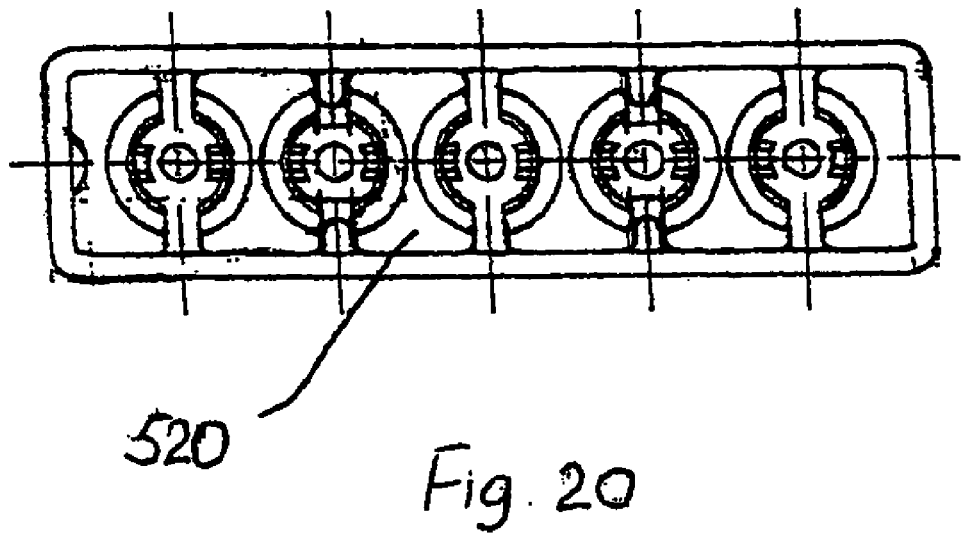
FIG. 20 is a close-up top view of an opening of a screw-receiving recess of a container of FIG. 14.

As best seen in FIGS. 14 and 15, the container 510 has a body shell 512 with five screw-receiving recesses 514a, 514b, 514c, 514d, and 514e, the details of which are illustrated in FIGS. 16-19. In common with the first and second embodiments, each screw-receiving recess is provided with a sleeve 511, and a pair of fingers 600a and 600b.

The body shell 512 has an open box configuration and includes an upper surface 513, two side surfaces 515a and 515b, a front surface 517a and a back surface 518a. The front and back surfaces 517a and 517b are provided with two pairs of opposite ribs 516a, 516b and 518a, 518b (not shown). The bottom portion 520 of the container 510 is left open to provide access for a sterilising medium.

As best seen in FIG. 15, to prevent breakage of the fingers 600a, 600b, the outer surfaces of the screw-receiving recesses 514a, 514b, 514c, 514d, and 514e are provided with frusto-conical portions 530a, 530b, 530c, 530d, and 530e terminating to the top surface 513.

Figure 21:
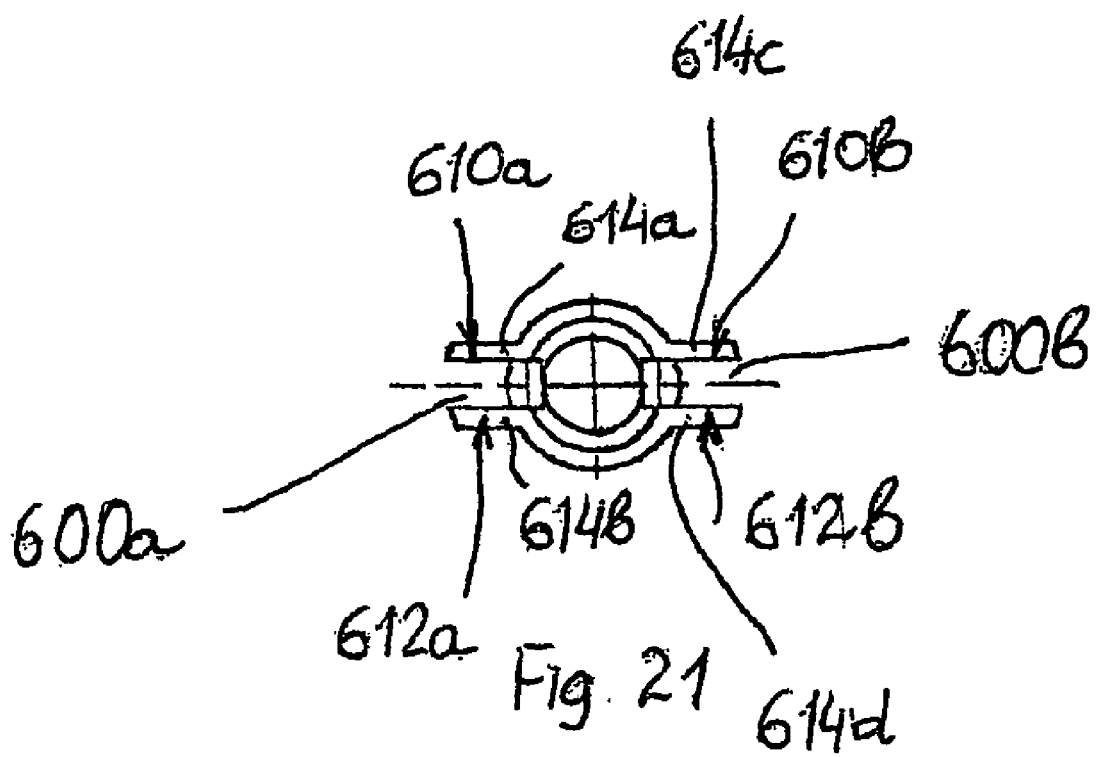
FIG. 21 is a bottom view of the container of FIG. 14.

Referring now to FIGS. 14 and 21, to facilitate the release of the screws from the screw-receiving recesses, longitudinal portions of side surfaces 610a, 612a and 610b, 612b of each of the fingers 600a, 600b are separated from the top surface 513 by two pairs of cuts 614a, 614b, and 614c, 614d provided on the upper surface 513 of the body shell 512.

Figure 22:
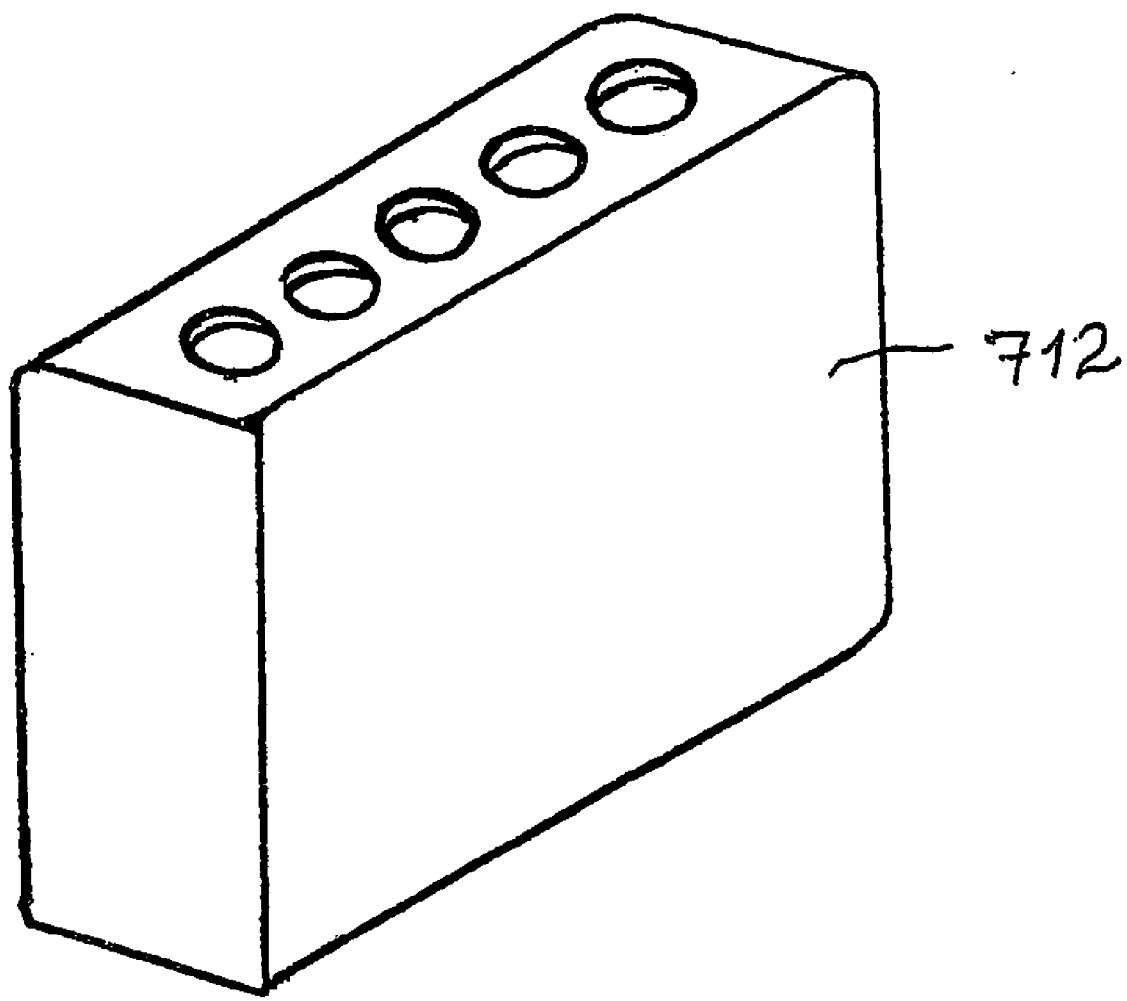
FIG. 22 is a perspective view of a body shell of a surgical screw container according to a fourth embodiment of the present invention.
Figure 23:
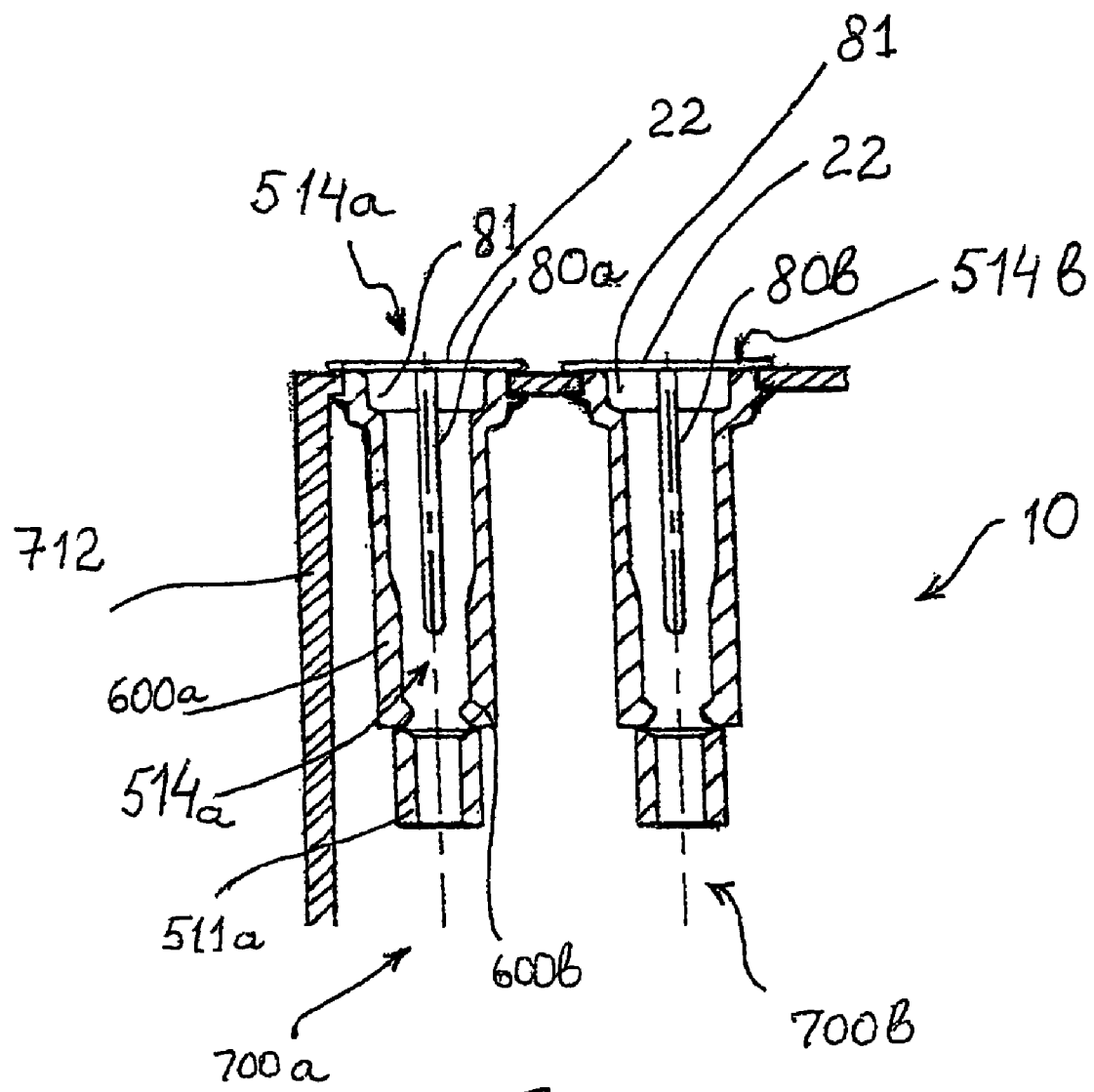
FIG. 23 is a partial cross-sectional view taken of the surgical screw container of FIG. 22.

As shown in FIGS. 22 and 23, a screw-receiving recess 514a, sleeve 511a, and fingers 600a and 600b can be manufactured as a stand-alone screw-holding unit 700a, 700b, separate from the body shell 712, and then attached to the body shell 712 during a succeeding manufacturing step. Although the embodiment illustrated in FIGS. 22 and 23 shows the screw-holding units arranged in-line, it will be appreciated by those skilled in the art that the orientation of the fingers in adjacent screw-holding units can be varied to achieve a more compact construction of the surgical screw container.

The container can be made of any appropriate polymeric material such as Polycarbonate, although other materials can be used.

It will be understood that the invention disclosed herein extends to alternative combinations of two or more of the individual features mentioned or evident from the text. All of these combinations constitute various alternative aspects of the invention.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, and all modifications which would be obvious to those skilled in the art are therefore intended to be embraced therein.

It will further be understood that any reference herein to known prior art does not, unless the contrary indication appears, constitute an admission that such prior art is commonly known by those skilled in the art to which the invention relates.

We claim:

1. A surgical screw container including
at least one recess which is adapted to receive therein a screw having a head and a threaded shank, said recess having an opening at one end to allow said screw to pass into or out of said recess, said recess being such that said screw lies within said recess with said head of said screw facing said opening,
retaining means for retaining said screw within said container, said retaining means being disposed within said recess and being releasable by insertion of a screwdriver shaft into said recess through said opening to allow withdrawal of said screw through said opening after said screw engages said screwdriver.

2. A surgical screw container according to claim 1 wherein said recess includes means to receive said shank.

3. A surgical screw container according to claim 1, wherein said recess includes a sleeve portion for imposing a radial constraint on said screw.

4. A surgical screw container according to claim 3 wherein said sleeve portion has a further opening which is smaller than the diameter of the head of the screw but larger than the diameter of the shank of the screw, said further opening having a longitudinal axis, said longitudinal axis being aligned with a longitudinal axis of said recess, and an abutting surface upon which the head of the screw rests.

5. A surgical screw container according to claim 1 wherein said retaining means includes at least one elastically flexible finger extending along a longitudinal axis within said recess.

6. A surgical screw container according to claim 5 wherein said finger has a free end provided with a lip and a contacting portion, said lip being oriented so as to engage a portion of said screw.

7. A surgical screw container according to claim 6 wherein said lip is adapted to engage the head of said screw to impose axial constraint on said screw.

8. A surgical screw container according to claim 6 wherein said lip is adapted to engage a thread on said threaded shank.

9. A surgical screw container according to claim 5 wherein said finger is movable away from a longitudinal axis of said recess upon said screwdriver shaft being urged toward said screw.

10. A surgical screw container according to claim 5 wherein said finger is formed in one piece with said recess.

11. A surgical screw container according to claim 5 wherein said at least one finger extends parallel to a longitudinal axis of the recess.

12. A surgical screw container according to claim 5 wherein said finger includes a front surface, a back surface, and two side surfaces, a portion of said finger terminating to a surface of said container, and wherein a longitudinal portion of each said side surface of said finger is separated from a corresponding surface of said recess.

13. A surgical screw container according to claim 1, further comprising two fingers disposed therewithin.

14. A surgical screw container according to claim 1, further comprising a plurality of fingers disposed therewithin.

15. A surgical screw container as claimed in claim 1, wherein there is included orientation means to hold said screw in a predetermined orientation relative to said recess once said screw is in said container.

16. A surgical screw container as claimed in claim 1, wherein said recess includes guide means to orient a screw driver relative to said recess.

17. A surgical screw container as claimed in claim 16 wherein said guide means includes an elongated groove to receive a mating projection on a screw driver.

18. A surgical screw container as claimed in claim 1, wherein said screw container is loaded with a screw by first loading said screw onto a jig which will hold said screw on said jig in a position which correspond to said at least one recess.

19. A surgical screw container as claimed in claim 18 wherein said jig also orients said screw in the desired orientation in which said screws are to be held in said container.

20. A surgical screw container as claimed in claim 18, wherein said jig has a maximum width which is less than twice the minimum distance from the centre of said recess to said retaining means.

21. A surgical screw container according to claim 1, wherein said container includes a body shell having an open box configuration for providing access for a sterilising medium.

22. A surgical screw container according to claim 1, wherein said container includes an upper surface, two opposite side surfaces, a front surface, a back surface, and an open bottom, and wherein said recess terminates at said upper surface.

23. A surgical screw container according to claim 1, wherein an outer periphery of a screw-receiving recess is provided with a frusto-conical region terminating to a surface of said surgical screw container.

* * * * *